United States Patent
Schmid et al.

(10) Patent No.: US 10,898,306 B2
(45) Date of Patent: Jan. 26, 2021

(54) DENTAL TREATMENT SYSTEM

(71) Applicant: 3M INNOVATIVE PROPERTIES COMPANY, St. Paul, MN (US)

(72) Inventors: Rudolf Schmid, Eichenau (DE); Stefan K. Welker, Geltendorf (DE); Korbinian Gerlach, Gauting (DE)

(73) Assignee: 3M Innovative Properties Company, St. Paul, MN (US)

( * ) Notice: Subject to any disclaimer, the term of this patent is extended or adjusted under 35 U.S.C. 154(b) by 134 days.

(21) Appl. No.: 16/462,975

(22) PCT Filed: Nov. 21, 2017

(86) PCT No.: PCT/US2017/062679
§ 371 (c)(1),
(2) Date: May 22, 2019

(87) PCT Pub. No.: WO2018/098107
PCT Pub. Date: May 31, 2018

(65) Prior Publication Data
US 2019/0374320 A1   Dec. 12, 2019

(30) Foreign Application Priority Data
Nov. 25, 2016   (EP) ..................................... 16200667

(51) Int. Cl.
*A61C 19/00*   (2006.01)
*A61C 13/15*   (2006.01)
(Continued)

(52) U.S. Cl.
CPC .......... *A61C 19/004* (2013.01); *A61B 1/0005* (2013.01); *A61B 1/24* (2013.01);
(Continued)

(58) Field of Classification Search
CPC ..... A61B 1/00009; A61B 1/0005; A61B 1/24; A61B 1/247; A61B 90/39;
(Continued)

(56) References Cited

U.S. PATENT DOCUMENTS 6,123,545 A   9/2000 Eggler
6,331,111 B1   12/2001 Cao
(Continued)

FOREIGN PATENT DOCUMENTS

CN   204902837   12/2015
CN   105300310   2/2016
(Continued)

OTHER PUBLICATIONS

International Search Report for PCT International Application No. PCT/US2017/062679, dated Feb. 14, 2018, 6 pages.

*Primary Examiner* — Matthew M Nelson

(57) ABSTRACT

A dental treatment system has a light irradiation device (2) and an image display (3). The light irradiation device has a polymerization light source (5a) for emitting blue light and a camera (6) for capturing a series of images. The system is set up for generating a first marker (11) and a second marker (20) superimposed with the images and to display the first marker (11) in a fixed positional relationship to an image pattern recognized in a first and in a second image of the series of images and to display the second marker (20) in a fixed positional relationship to an image area underlying the images.

12 Claims, 3 Drawing Sheets

(51) Int. Cl.
*A61B 90/00* (2016.01)
*A61B 1/00* (2006.01)
*A61B 1/24* (2006.01)
*G06T 7/00* (2017.01)

(52) U.S. Cl.
CPC ............ *A61B 90/39* (2016.02); *G06T 7/0016* (2013.01); *A61B 2090/3912* (2016.02); *A61B 2090/3937* (2016.02); *G06T 2207/30036* (2013.01); *G06T 2207/30204* (2013.01)

(58) Field of Classification Search
CPC ...... A61B 2034/2048; A61B 2090/309; A61B 2090/3612; A61B 2090/3912; A61B 2090/3937; A61C 19/004; G06T 7/0016; G06T 2207/30036; G06T 2207/30204
USPC ..................................................... 433/27, 29
See application file for complete search history.

(56) References Cited

U.S. PATENT DOCUMENTS

| | | | |
|---|---|---|---|
| 6,719,558 B2 | 4/2004 | Cao | |
| 6,719,559 B2 | 4/2004 | Cao | |
| 6,755,648 B2 | 6/2004 | Cao | |
| 6,755,649 B2 | 6/2004 | Cao | |
| 6,780,010 B2 | 8/2004 | Cao | |
| 6,783,362 B2 | 8/2004 | Cao | |
| 6,799,967 B2 | 10/2004 | Cao | |
| 6,824,294 B2 | 11/2004 | Cao | |
| 6,910,886 B2 | 6/2005 | Cao | |
| 6,926,524 B2 | 8/2005 | Cao | |
| 6,929,472 B2 | 8/2005 | Cao | |
| 6,932,600 B2 | 8/2005 | Cao | |
| 6,953,340 B2 | 10/2005 | Cao | |
| 6,955,537 B2 | 10/2005 | Cao | |
| 6,969,253 B2 | 11/2005 | Cao | |
| 6,971,875 B2 | 12/2005 | Cao | |
| 6,971,876 B2 | 12/2005 | Cao | |
| 6,974,319 B2 | 12/2005 | Cao | |
| 6,979,193 B2 | 12/2005 | Cao | |
| 6,979,194 B2 | 12/2005 | Cao | |
| 6,981,867 B2 | 1/2006 | Cao | |
| 6,988,890 B2 | 1/2006 | Cao | |
| 6,988,891 B2 | 1/2006 | Cao | |
| 7,066,732 B2 | 6/2006 | Cao | |
| 7,077,648 B2 | 7/2006 | Cao | |
| 7,086,585 B2 | 8/2006 | Cao | |
| 7,094,054 B2 | 8/2006 | Cao | |
| 7,108,504 B2 | 9/2006 | Cao | |
| 7,294,364 B2 | 11/2007 | Cao | |
| 8,231,383 B2 | 7/2012 | Gill | |
| 9,817,367 B2 | 11/2017 | Reinhardt | |
| 2005/0095551 A1* | 5/2005 | Taub | A61C 9/0053 433/24 |
| 2009/0021745 A1* | 1/2009 | Tamura | A61B 5/0059 356/479 |
| 2010/0091112 A1 | 4/2010 | Veeser | |
| 2012/0237890 A1* | 9/2012 | Liang | G01N 21/4795 433/29 |
| 2012/0249595 A1 | 10/2012 | Feinstein | |
| 2013/0330684 A1 | 12/2013 | Dillon | |
| 2015/0250572 A1* | 9/2015 | Gramann | A61B 1/247 433/29 |
| 2016/0026264 A1 | 1/2016 | Cheng | |
| 2016/0051345 A1* | 2/2016 | Levin | A61C 9/0053 433/29 |
| 2019/0374320 A1* | 12/2019 | Schmid | A61B 1/24 |

FOREIGN PATENT DOCUMENTS

| | | | |
|---|---|---|---|
| JP | 2008086554 | 4/2008 | |
| JP | 2013-0132062 | 1/2013 | |
| RU | 36208 | 3/2011 | |
| RU | 2 538 614 | 8/2013 | |
| WO | 2014-043488 | 3/2014 | |
| WO | WO-2014043488 A1 * | 3/2014 | ............... A61B 1/24 |
| WO | 2016-164238 | 10/2016 | |
| WO | WO-2016164238 A1 * | 10/2016 | ........... A61B 5/7455 |

\* cited by examiner

DENTAL TREATMENT SYSTEM

FIELD OF THE INVENTION

The invention relates to a dental treatment system that has a light irradiation device and an image display. The light irradiation device has a motion control function based on a first marker that (virtually) sticks to an object captured by the camera while the camera is eventually moved relatively to the object.

BACKGROUND ART

Light hardenable or light curable materials are widely used in dentistry for the restoration of teeth. Such materials typically can be placed to a patient's tooth precisely and conveniently before they are hardened in place instantly. Light hardenable materials often include a polymerizable matrix material and filler materials including colorants, and may initially be generally soft or flowable so that they can be applied in a desired location and shape. For example, for restoration of a tooth the dental material may be filled into a tooth cavity and shaped so that the restored tooth resembles a natural tooth. Once the desired shape has been formed, the material may be cured by exposing it to light of a desired wavelength. The light typically activates photoinitiators in the dental material that cause the matrix material to polymerize.

The use of dental materials that are hardenable by blue light of a wavelength of between about 450 and 500 nm (nanometers) has become common in dentistry. Accordingly, light-emitting devices used for hardening such dental materials typically emit light at such wavelengths. Such a light-emitting device is for example available from 3M Deutschland GmbH, Germany, under the trade designation Elipar™ S10.

An important aspect in the use of light hardenable dental material is the appropriate hardening of the dental material. As a requirement for an appropriate hardening the dental material needs to be exposed to the blue light at a sufficient intensity and duration. There exist some light devices which have functions to support appropriate hardening of dental materials.

For example, WO 2014/043488 A1 discloses a dental irradiation device which is adapted to recognize the distance between the device and an object for automatically adjusting the light intensity of the light irradiated from the light device.

Further WO 2016/164238 A1 discloses a dental light irradiation device which has sensing means for sensing a change of a position of the device and an indicator for physically indicating the position change.

Although existing devices have certain advantages there is still a need for a device which helps is reliability and appropriately hardening dental materials. Further it is still desirable to provide a device that allows easy handling for appropriately hardening dental materials in different situations.

SUMMARY OF THE INVENTION

The invention relates to a dental treatment system. The dental treatment system comprises at least a light irradiation device and an image display. The light irradiation device comprises a polymerization light source for emitting blue light and a camera for capturing a series of images. Additionally, the system comprises a control unit that is connected to the camera for receiving the images from the camera. The control unit is set up for generating a first and a second marker superimposed with the images. The control unit is further set up to drive the system to display the first marker superimposed with the images. In particular, the first marker is superimposed with the images in a fixed positional relationship to an image pattern recognized in a first and in a second image of the series of images. The control unit is further set up to drive the system to display the second marker superimposed with the images in a fixed positional relationship to an image area underlying the images.

The invention is advantageous in that it facilitates the positioning of dental light irradiation devices. In particular, it has been found that the positioning a light irradiation device is most accurate just upon activating the polymerization light source. This is because a dentist typically positions the light irradiation device visually in a patient's mouth. Once the polymerization light has been activated the attention of the dentist with respect to the position of the light irradiation device may decrease. This is because the polymerization time last over several seconds up to 20 seconds. The invention facilitates the positioning because it memorizes the initial position of the light irradiation device and optically indicates a displacement of the light irradiation device away from that initial position.

In one embodiment, the light irradiation device further comprises an illumination light source. The illumination light source may comprise at least one white LED. The illumination light source enables the capturing of images by the camera independent of natural ambient light.

For the purpose of the present specification the term "blue light" refers to light having a wavelength within the range of about 430 nm to 500 nm, preferably within a range of about 430 nm to 480 nm. For the purpose of the present specification the term "white light" refers to light having a wavelength within a range of about 380 nm to 780 nm. Although white light may also comprise light at wavelengths overlapping with the range of wavelengths of blue light, white light preferably does not predominantly consist of light within the range of blue light but has significant portions of visible light at wavelengths outside the range of blue light. In contrast blue light preferably predominantly consists of light within a range of about 430 nm to 480 nm. Blue light may particularly not comprise light having a wavelength outside the range of about 430 nm to 480 nm at a substantial intensity or at all. In particular blue light may have a first portion of light within a range of about 430 nm to 480 nm and preferably does not have a significant second light portion within a range of 570 nm and 590 nm, wherein the maximum intensity of the second portion of light is preferably less than 10% and more preferably less than 1% of the maximum intensity of the first portion of light. Further blue light may not have a significant third light portion within the spectrum of visible light outside the range of 430 nm and 480 nm and outside the range of 570 nm to 590 nm, wherein the maximum intensity of any third portion of light is preferably less than 25% and more preferably less than 20% of the maximum intensity of the first portion of light.

In one embodiment, the control unit has functionality to generate the first and second marker and to superimpose the first and second marker with an image of the series of images. The superimposition may be based on data, for example in the form of a bitmap. In particular the image may by captured and processed as a bitmap and the control unit may combine the bitmap of the image with a bitmap of the first marker. Such a combination may be performed, for example, based on a logic operation in which some of the data in the image bitmap is replaced or modified by the bitmap of the first or the second marker.

In one embodiment, the position of the image pattern in the first image relative to the image area of the first image is different than the position of the image pattern in the second image relative to the image area of the second image. The image area typically corresponds to an area that can be captured by the camera. For example, the image area may be a rectangular section. All images taken by the camera may be based on the same image area. Typically, the image area is defined by the size of the image sensor (for example the CCD or CMOS circuit) in combination with the optics implemented in the camera.

In a further embodiment, the control unit is set up for monitoring the position of the image pattern relative to the image area by performing the steps of:
  determining the image pattern in the first image based on first image information;
  recognizing the image pattern in a second image based on second image information that are at least similar to the first image information; and
  determining an offset between the positon of the image pattern in the first image and the position of the image pattern in the second image relative to the image area of the first and the second image, respectively.

By determination of any offset of the same image pattern in the first and the second image a relative movement of the light irradiation device to an object captured in the images can be detected. The relative movement can be indicated by the first and second marker displayed at an offset to each other. Therefore, a user can recognize the relative movement and reposition the light irradiation device accordingly. Thus, the present invention provides a motion control function for the light irradiation device.

In one embodiment, the light irradiation device comprises an acceleration sensor. The acceleration sensor is preferably configured for measuring linear and/or rotational accelerations light irradiation device and for providing an output that comprises information about the magnitude and the direction of the acceleration measured. The recognition of the image pattern in the second image may be supported by using the output of the acceleration sensor. In particular the measured magnitude and/or direction of the acceleration may be used to calculate an expected position of the image pattern in the second image. The expected position may differ (slightly) from the actual position of the image pattern. However, the process of recognizing the image pattern in the second image is facilitated if the recognition starts based on the expected position rather than a fixed predetermined position in the image or the previous position of the image pattern. Accordingly, the processing time for the pattern recognition process can be minimized.

In an embodiment, the dental treatment system is operable in a first operation mode in which the polymerization light source is switched off and the camera is switched on, or in a second operation mode in which both, the polymerization light source and the camera, are switched on. Accordingly, the light irradiation device may be either deactivated (the polymerization light source and the camera are switched off) or the light irradiation device may be operated in the first or the second operation mode. The light irradiation device may have further operation modes, for example a third operation mode in which the camera is switched off and the polymerization light is switched on. Such a third operation mode would allow the device to be operated similar to conventional light irradiation devices.

In a further embodiment activating the second operation mode triggers the image pattern to be recognized. In particular upon activating the second operation mode the camera may capture first image. Based on the first image the image pattern may be derived.

The "image pattern" as referred to herein is preferably a general characteristic of an image, for example a two-dimensional statistical evaluation of a color landscape or light/dark areas.

For example, a particular color landscape in a subsection of one image may be present also in another image. Whether two images comprise the same image pattern can be determined by matching. Matching is known in the field of image processing and can be performed based on various principles. For example, a particular subsection of one image may be compared with several particular subsections of another image according to an algorithm. During the comparison tolerances between the individual image information in the two subsections may be permitted. Although in this example—technically—two image patterns are actually compared these two image patterns have one single general image pattern in common. The common image pattern in the example is based on the tolerances used for the comparison. In another example, a color or light/dark landscape in a subsection of one image may be standardized, for example converted into black and white, and compared to a standardized subsection of another image. Thereby the exact transitions between any black and white areas may be omitted to account for tolerances. Other implementations of image pattern recognition are possible.

In a further embodiment in the second operation mode the first marker is displayed superimposed with the images in a fixed positional relationship to the image pattern in the images and the second marker is displayed superimposed with the images in a fixed positional relationship to the image area of the images. Accordingly, in the second operation mode the first marker sticks with the image pattern while the second marker is fixed relative to the image area. This means that the first marker follows the object that was initially captured by the camera while the second marker follows a movement of the light irradiation device. Thus, a user can recognize if the light irradiation device moves away from the initial position and can reposition it accordingly.

In an embodiment, the polymerization light source and the camera are oriented such that an object illuminated by the polymerization light source and/or the illumination light source can be captured by the camera.

In a further embodiment in the first operation mode the first marker and the second marker are displayed superimposed with the images in a fixed positional relationship to the image area of the images. This means the in the first operation mode the first marker does not stick at the object captured initially.

In one embodiment, one or both of the first and second marker have a first appearance in the first operating mode and a different second appearance in the first operating mode. The first and second appearances may be characterized by different colors. The first marker may be based on a peripheral contour. Further, the second marker may be based on a pointer. The first marker may be a circle, ellipse or rectangle, and the second marker may be a point or crosshair.

DETAILED DESCRIPTION OF THE INVENTION

Figure 1:
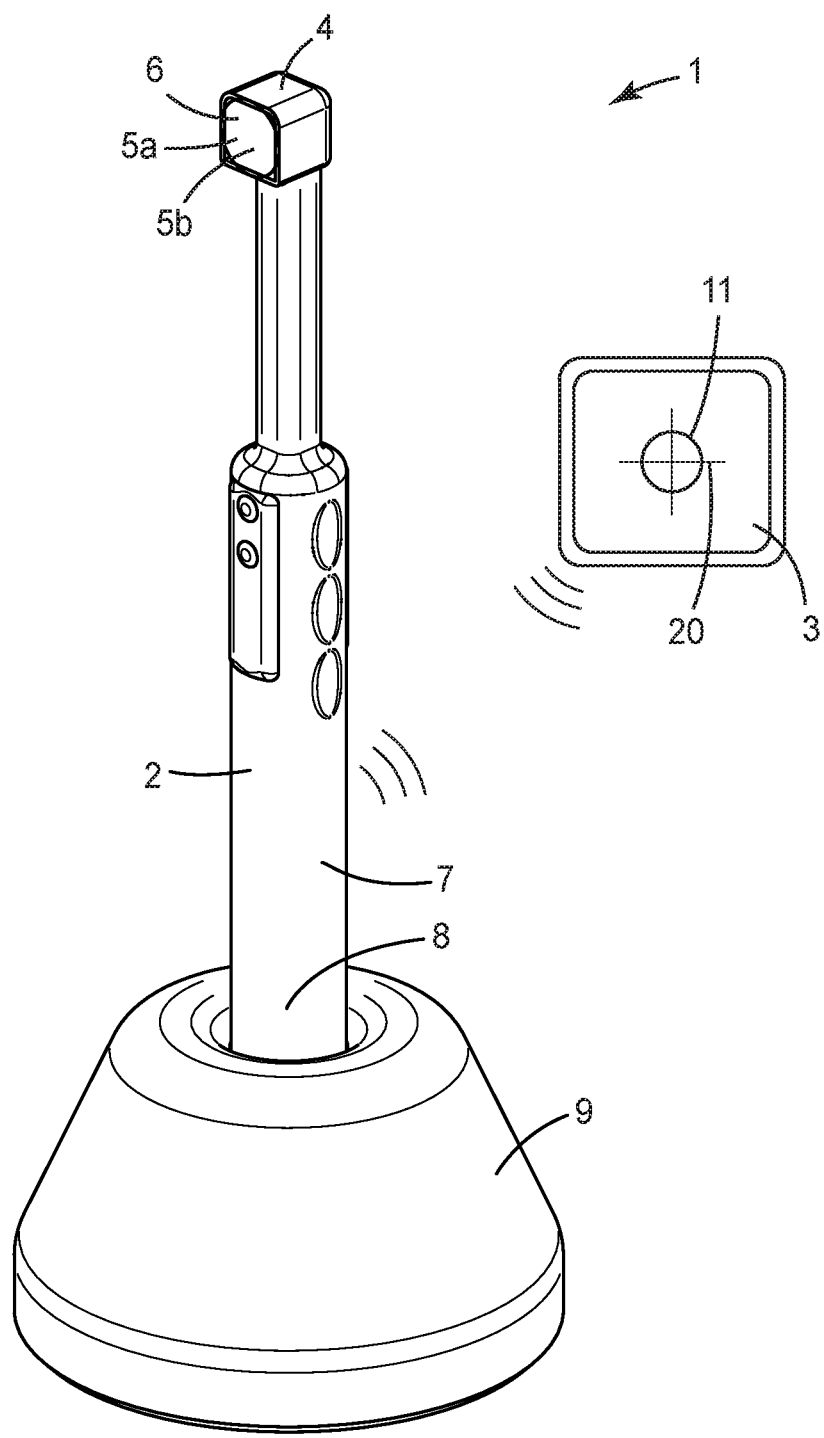
FIG. 1 is a perspective view of a light irradiation device according to an embodiment of the invention.

FIG. 1 shows a dental treatment system 1 which has a light irradiation device 2 and an image display 3. The image display may be in the form of a tablet computer for example. The light irradiation device 2 has front portion 4 in which a polymerization light source 5a and an illumination light source 5b accommodated. The polymerization light source 5a in the example is a blue LED which emits blue light, when switched on, and the illumination light source is a white LED which emits white light, when switched on. Within the front portion 4 further a camera 6 is accommodated. The camera 6 may be a CCD or CMOS based camera.

The system has further a control unit 7 which in the example is integrated within the light irradiation device 2. However, the control unit (or parts of the control unit) may further be arranged within the image display 3 or in a device separate from the light irradiation device 2 and the image display 3. The control unit 7 comprises electronic circuitry and software for controlling the operation of the light irradiation device 2. The control unit 7 further comprises a wireless communication interface for enabling communication with a wireless network and/or a wireless communication interface of the image display 3.

The control unit 7 is connected to the camera 6 for receiving images captured by the camera 6. The control unit is further set up for generating a first and a second marker 11, 20 superimposed with the images displayed in the image display 3. The image or images taken by the camera together form an optical output that is displayed via the image display 3.

The light irradiation device 2 in the example is an overall wireless device. This means that the light irradiation device 2 has a rechargeable battery 8 (not visible). For charging the battery 8 a charging device 9 is provided by which the battery 8 can be charged. For charging the battery 8 the light irradiation device 2 can be received on the charging device 9 as illustrated. For use the light irradiation device 2 can be removed from the charging device 9. In the example, the energy for charging the battery is provided by a contactless interface, for example by induction. Contact-based charging is however likewise possible.

Figure 2:
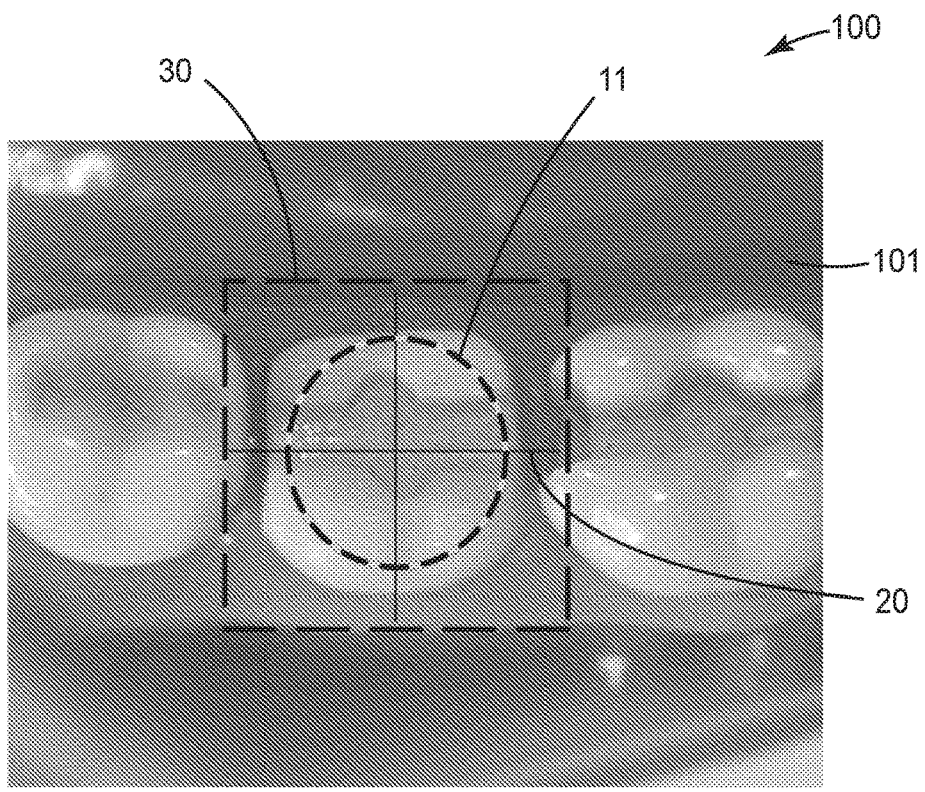
FIGS. 2 to 5 are illustrations of images superimposed with a first and a second marker as provided by the light irradiation device according to an embodiment of the invention.

FIG. 2 shows an optical output 100 as provided by a dental treatment system operating in a first operation mode in which the camera is switched on and in which the polymerization light source is switched off. To enable the camera for capturing images independent from ambient light conditions the illumination light source is switched on too. The output 100 comprises an image 101 superimposed by a first marker 11 and a second marker 20. In the example, the image 101 captured by the camera is a portion of a patient's dentition. The image 101 particularly shows three teeth of the patient. It is noted that the image 101 captured by the camera depends on the positioning of the device (or camera) relative to the patient, so that an image in other examples may look different. In the example the first marker 11 is in the form of a circle. In the first operation mode the first marker 11 is displayed at a first format. In the example, the first marker 11 is displayed grey (indicated in the Figure by a dashed line) for indicating that the light irradiation device operates in the first operation mode in which the polymerization light source is switched off. Further, the second marker 20 is displayed in the form of cross-hairs. The second marker is displayed at a second format. In the example, the second marker 20 is displayed black. The skilled person will recognize that alternative colors or shapes for the first and second format of the first and marker 11, 20, respectively are likewise possible. The second marker 20 indicates a center of a light beam emitted from the second light source. In the example, the second marker 20 also indicates a center of an image area of the camera. Accordingly, the second marker 20 marks the position at which the center of the light beam will impinge on an object captured by the camera.

In the first operation mode the first and second marker 11, 20 are aligned with each other. In the example, the center of the circle is positioned on the intersection of the cross-hairs. In the first operation mode, a movement of the light irradiation device (and the camera) relative to the patient does not cause any change of the relative position between the first and second marker 11, 20.

Figure 3:
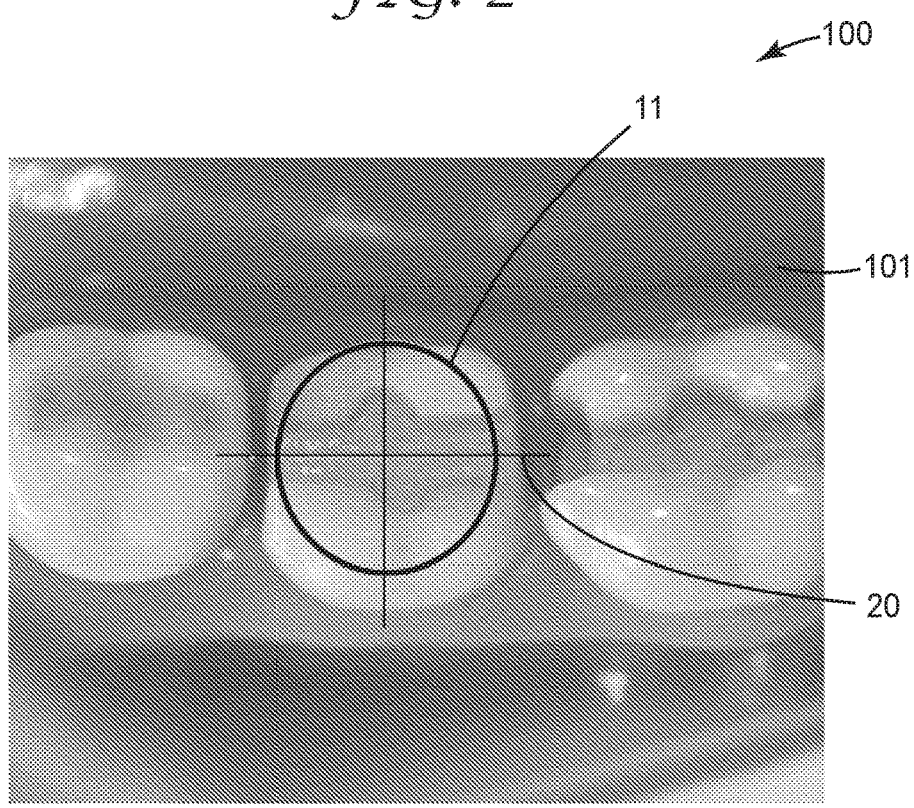

FIG. 3 shows the optical output 100 at a second operation mode of the light irradiation device. In the second operation mode, the camera and the polymerization light source are switched on. The activation (switching on) of the second operation mode (for example by a user pushing a button on the light irradiation device) triggers the light irradiation device to initiate an image pattern recognition based on an image taken in association with the activation of the second operation mode. There are various ways to perform a image pattern recognition. In one example a image pattern may be derived from an initial image 101 taken from an object, for example from a portion of a patient's dentition. In the example, the initial image 101 looks like the image illustrated if FIG. 2 because the light irradiation device was not moved during activating the second operation mode. The image pattern may be based on general characteristics of the initial image 101, for example a two-dimensional statistical evaluation of a color landscape or light/dark areas. Although more sophisticated image pattern recognition methods are known and applicable it is preferred to use relatively simple image pattern recognition methods to minimize computing time for image pattern recognition and matching.

Upon activating the second operation mode the initial image 101 may be captured and optionally stored in a memory of the control unit. Further, the first marker 11 is displayed superimposed with the initial image 101 and aligned with the second marker 20. At this stage, the first marker 11 is displayed green (indicated in the Figure by a continues line) for indicating that the light irradiation device operates in the second operation mode. Further, the green color indicates that the light irradiation device has not significantly moved in position relative to the position at which the second operation mode was activated.

In the initial image 101 the relatively bright areas representing the patient's teeth surrounded by the relatively dark area representing the patient's gums form a suitable basis for recognizing an image pattern. In the example, the image pattern is a two-dimensional statistical evaluation of light and dark areas in the whole initial image 101 or in a image pattern recognition window 30 defined within the initial image 101. The size and shape of the image pattern recognition window 30 may be pre-determined in the light irradiation device or may be adjustable by a user. The recognized image pattern may be stored as a reference image pattern. Further, the position of the image pattern relative to the image may be stored as an initial position of the image pattern. The position of the image pattern may for example be defined (in a bitmap or two-dimensional matrix) by the left most point and the upper most point relative to the left upper corner of the image. Other reference points may be used though, as appropriate.

Figure 4:
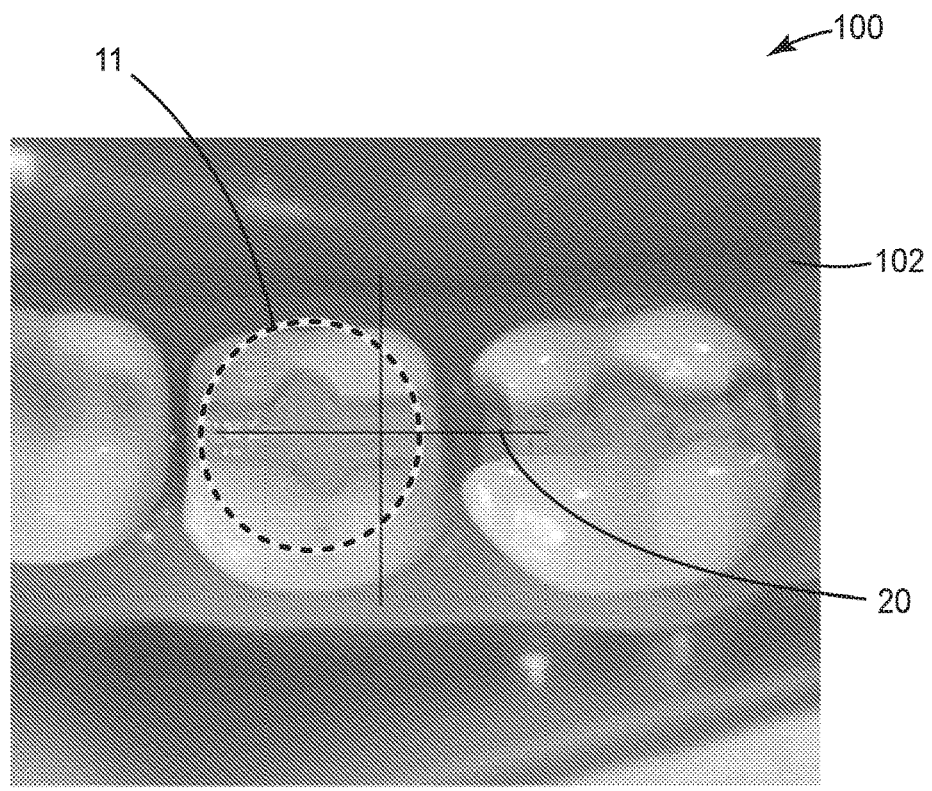

FIG. 4 shows a situation in which the light irradiation device has been moved slightly toward the right. The light irradiation device is configured for continuously taking further images via the camera at least in the second operation mode. In the example, a second image 102 is taken form a portion the patient's dentition. Further, an image recognition is automatically initiated upon the second image 102 is taken. This second image 102 is evaluated for the presence of a image pattern which corresponds to the reference image pattern. In other words, it is checked whether the image pattern that was recognized in the initial image 101 is also present or at least partially present in the second image 102. Several ways of checking whether the same image pattern is (at least partially) present in the first and second image 101, 102 are possible. According to one way a image pattern may be recognized also in the second image 102 and that second image pattern may be matched with the reference image pattern recognized from the initial image 101. If the matching is successful the same image pattern is present in the initial and the second image 101, 102. As shown in the example the tooth in the middle of the three teeth in the second image 102 shown is offset further to the left with respect to the initial image 101. This is due to the light irradiation device (or camera) is moved toward the right. Nevertheless, the initial image 101 and the second image 102 partially match with one another. This means that the initial image 101 and the second image 102 exhibit the same image pattern. For example, an area around the middle of the three teeth is the same in both, the initial and the second image 101, 102. The offset between the initial and the second image 101, 102 can be calculated by determining the position of the image pattern in the second image 102 and by determining the difference between the position of the image pattern in the initial and the second image 101, 102. It is noted that the determination of the offset between the positions of the image pattern in the initial and the second image 101, 102 can be performed based on a comparison of the position of the image pattern determined in the second image 102 and the stored position of the image pattern in the stored initial image 101. Further, the determination of the position of the image pattern in both, the initial and the second image 101, 102, may be performed based on a stored initial image 101. Other possibilities to determine an offset between two images with overlapping content may be used as appropriate. As shown the first marker 11 in the second image 102 is positioned at the same position of the middle tooth of the three teeth as in the first image 101. Accordingly, the first marker 11 is displayed in the first and second image in a fixed positional relationship to the same image pattern present in the first and second image 101, 102, although the image pattern is offset in the first and second image 101, 102. In other words, the dental treatment system is configured such that the first marker 11 during a movement of the light irradiation device sticks with the image pattern while the second marker sticks with the position of the camera. Thereby a user can recognize and control the position of the light irradiation device relative to an object (in particular a tooth to be restored with light polymerizable or hardenable dental material) during operating the light irradiation device in the second operation mode (in particular during exposing the light hardenable dental material by blue light emitted from the polymerization light source). The polymerization of dental materials may take several seconds up to 20 seconds so that keeping the device at the same position over such durations is difficult. The display of the first and second marker 11, 20 enable a user to easily recognize and correct any offset between an initial position of the light irradiation device and further positions over time. Thus, the light irradiation device can be maintained at a desired position that ensures appropriate polymerization of the light hardenable dental material.

In the situation illustrated in FIG. 4 the light irradiation device is displaced relative to the situation shown in FIG. 3 at extent that is not acceptable for appropriately hardening a light hardenable dental material (not shown) that may be placed in tooth shown. Accordingly, the first marker 11 is turned from a green to a yellow color (as indicated in the Figure by a dotted line). Thus, a user can immediately recognize that an inacceptable displacement of the light irradiation device has occurred. Optionally the dental treatment system may be configured to provide an audible and/or tactile signal upon an inacceptable displacement of the light irradiation device being detected. Further, optionally the dental treatment system may be configured to reduce the light intensity upon an inacceptable displacement of the light irradiation device being detected.

Figure 5:
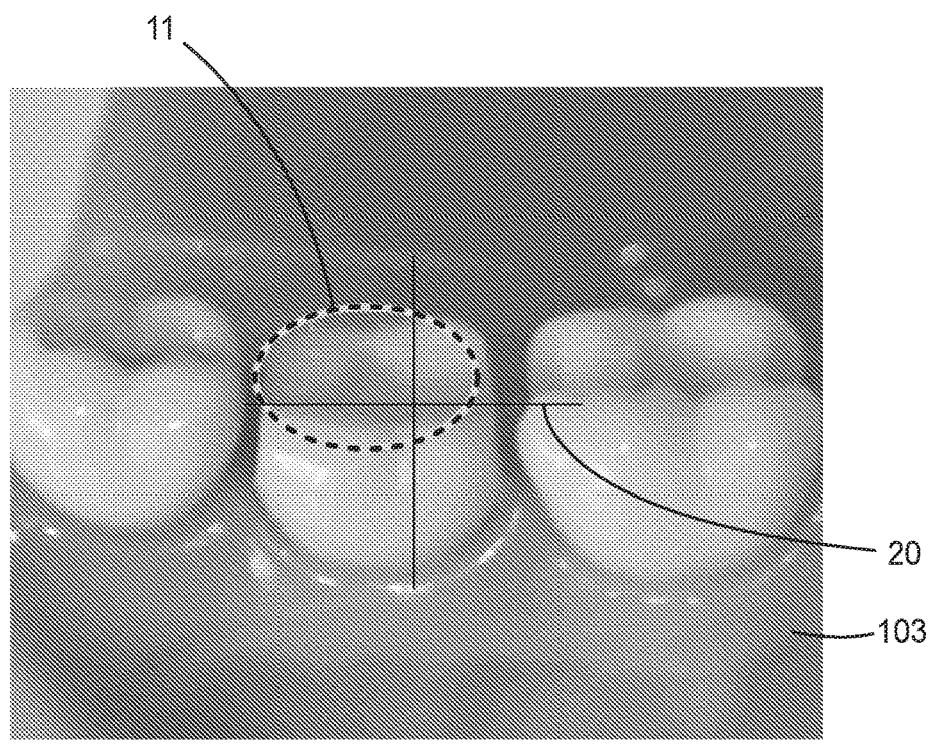

FIG. 5 illustrates a situation in which the light irradiation device was skewed relative to the patient's dentition. In the example, the image pattern recognition is based on three-dimensional image recognition as for example used in intra-oral scanners. It is possible to derive a three-dimensional image from two or more two-dimensional images taken from the same three-dimensional object from different (geometric) perspectives. Thus, it is also possible to assign each of the two-dimensional images that were used as a basis for calculating the three-dimensional image a viewing angle and even a distance relative to the three-dimensional image. Accordingly, any image patterns recognized in the two-dimensional images can be matched based on the information about the viewing angle and distance. After a transformation based on the viewing angle and distance the image patterns may be matched as described in the example of FIG. 4. Further, as shown in FIG. 5 the first marker can be displayed in the appropriate perspective to the image 103. Because the first marker 11 originally is a circle any deformation toward an ellipse indicates that the light irradiation device was skewed. In the example shown the light irradiation device was not only skewed but also laterally displaced at an inacceptable extent so that the first marker 11 is displayed in a yellow color.

In the example, upon deactivating the second operation mode the image pattern recognition is reset. In particular, the image pattern recognized from the initial image 101 may be erased or may be replaced by a new image pattern upon reactivation of the second operation mode.

What is claimed is:

1. A dental treatment system comprising a light irradiation device and an image display, the light irradiation device comprising a polymerization light source for emitting blue light and a camera for capturing a series of images, wherein the system comprises a control unit that is connected to the camera for receiving the images from the camera, the control unit further being set up for generating a first and a second marker superimposed with the images, and wherein the control unit is further set up to drive the system to display the first marker superimposed with the images in a fixed positional relationship to an image pattern recognized in a first and in a second image of the series of images, and wherein the control unit is further set up to drive the system to display the second marker superimposed with the images in a fixed positional relationship to an image area underlying the images.

2. The dental treatment system of claim 1, wherein the position of the image pattern in the first image relative to the image area of the first image is different than the position of the image pattern in the second image relative to the image area of the second image.

3. The dental treatment system of claim 1, wherein the control unit is set up for monitoring the position of the image pattern relative to the image area by performing the steps of:
   determining the image pattern in the first image based on first image information;
   recognizing the image pattern in a second image based on second image information that are at least similar to the first image information; and
   determining an offset between the position of the image pattern in the first image and the position of the image pattern in the second image relative to the image area of the first and the second image, respectively.

4. The dental treatment system of claim 1, being operable in a first operation mode in which the polymerization light source is switched off and the camera is switched on, or in a second operation mode in which both, the polymerization light source and the camera, are switched on.

5. The dental treatment system of claim 4, wherein activating the second operation mode triggers the image pattern to be recognized.

6. The dental treatment system of claim 5, wherein in the second operation mode the first marker is displayed superimposed with the images in a fixed positional relationship to the image pattern in the images and the second marker is displayed superimposed with the images in a fixed positional relationship to the image area of the images.

7. The dental treatment system of claim 4, wherein in the first operation mode the first marker and the second marker are displayed superimposed with the images in a fixed positional relationship to the image area of the images.

8. The dental treatment system of claim 4, wherein one or both of the first and second marker have a first appearance in the first operating mode and a different second appearance in the second operating mode.

9. The dental treatment system of claim 8, wherein the first and second appearances are characterized by different colors.

10. The dental treatment system of claim 1, wherein the first marker is based on a peripheral contour, and wherein the second marker is based on a pointer.

11. The dental treatment system of claim 10, wherein the first marker is a circle, ellipse or rectangle, and wherein the second marker is a point or crosshair.

12. The dental treatment system of claim 1, wherein the light irradiation device comprises an acceleration sensor that is configured for measuring linear and/or rotational accelerations of the light irradiation device and for providing an output that comprises information about the magnitude and the direction of the acceleration measured, wherein the measured magnitude and/or direction of the acceleration is used to calculate an expected position of the image pattern in the second image.

* * * * *